(12) United States Patent
Saini

(10) Patent No.: US 10,071,254 B2
(45) Date of Patent: Sep. 11, 2018

(54) OPTICALLY BASED DEVICES, SYSTEMS, AND METHODS FOR NEUROMODULATION STIMULATION AND MONITORING

(71) Applicant: Zyvex Labs, LLC, Richardson, TX (US)

(72) Inventor: Rahul Saini, Allen, TX (US)

(73) Assignee: Zyvex Labs, LLC, Richardson, TX (US)

( * ) Notice: Subject to any disclaimer, the term of this patent is extended or adjusted under 35 U.S.C. 154(b) by 0 days.

(21) Appl. No.: 15/091,740

(22) Filed: Apr. 6, 2016

(65) Prior Publication Data

US 2016/0287885 A1    Oct. 6, 2016

Related U.S. Application Data

(60) Provisional application No. 62/143,500, filed on Apr. 6, 2015.

(51) Int. Cl.
| | |
|---|---|
| *A61N 1/37* | (2006.01) |
| *A61N 1/378* | (2006.01) |
| *A61N 1/36* | (2006.01) |
| *H04B 10/00* | (2013.01) |
| *H04B 13/00* | (2006.01) |
| *H02J 50/30* | (2016.01) |
| *A61N 1/372* | (2006.01) |

(52) U.S. Cl.
CPC ......... *A61N 1/3787* (2013.01); *A61N 1/3605* (2013.01); *A61N 1/37217* (2013.01); *H02J 50/30* (2016.02); *H04B 10/00* (2013.01); *H04B 13/005* (2013.01); *A61N 1/37223* (2013.01)

(58) Field of Classification Search
CPC ................ A61N 1/3787; A61N 1/3605; A61N 1/37217; A61N 1/37223; H02J 50/30; H04B 10/00; H04B 13/005
See application file for complete search history.

(56) References Cited

U.S. PATENT DOCUMENTS

| | | | | |
|---|---|---|---|---|
| 5,320,098 | A * | 6/1994 | Davidson ............. | A61N 5/0601 128/908 |
| 2004/0015211 | A1* | 1/2004 | Nurmikko ............ | A61B 5/0031 607/61 |
| 2004/0026604 | A1* | 2/2004 | Nishikawa ............. | H04J 14/02 250/214 R |

\* cited by examiner

*Primary Examiner* — Paula J Stice
(74) *Attorney, Agent, or Firm* — Haynes and Boone, LLP

(57) ABSTRACT

Devices, systems, and methods for neuromodulation are provided. For example, a neuromodulation system is disclosed that comprises an implantable neuromodulation module having a photodiode configured to generate electrical current in response to receiving light from an optical fiber; an optical transceiver; and at least one electrode configured to provide electrical stimulation to a nerve utilizing the electrical current generated by the photodiode. As another example, a method of neuromodulation is disclosed that comprises receiving light at a photodiode of a neuromodulation module and generating electrical current in response to receiving the light; and providing, via at least one electrode of the module positioned within the patient, electrical stimulation to a nerve of the patient utilizing the electrical current generated by the photodiode.

21 Claims, 14 Drawing Sheets

OPTICALLY BASED DEVICES, SYSTEMS, AND METHODS FOR NEUROMODULATION STIMULATION AND MONITORING

CROSS-REFERENCE TO RELATED APPLICATIONS

This application claims priority to and the benefit of U.S. Provisional Patent Application No. 62/143,500, filed Apr. 6, 2015, which is hereby incorporated by reference in its entirety.

TECHNICAL FIELD

The present disclosure relates to neuromodulation and, more particularly, to devices, systems, and methods for electrically stimulating nerve(s), blocking nerve signaling, and/or monitoring nerve activity.

BACKGROUND

Neuromodulation continues to increase as an adopted technique for treating of a wide variety of medical conditions. For example, neuromodulation devices for spinal cord stimulation have been utilized for the management of pain. Similarly, neuromodulation devices for deep brain stimulation have been utilized for the treatment of Parkinson's, essential tremor, dystonia, and other disorders. Neuromodulation devices for vagus nerve stimulation have been utilized to control seizures, such as those associated with epilepsy. Also, neuromodulation devices for renal nerve stimulation have been utilized to control blood pressure.

Existing neuromodulation systems typically require a surgical procedure to implant one or more electrodes at a desired location within a patient. Conductors then lead from the electrodes to a power source and pulse generator. The power source, such as a battery, can be implanted along with the electrodes. However, if the power source becomes disconnected, stops holding a charge, or otherwise stops working properly, a further surgery is required to replace the power source. To eliminate this issue, the conductors may lead from the electrodes to a power source positioned outside of the body. However, this approach requires an opening through the skin that can be uncomfortable for the patient, prone to infection, and prone to causing scar tissue along the length of the conductors within the patient. Further, the longer the distance the conductors have to extend between the power source and the electrodes, the greater the amount of power that is required to be provided to account for the increased attenuation of the electrical signal along the length of thin conductors, which are preferred or, in some cases, required for patient comfort and/or access to the desired stimulation site. Also, the electrode leads need to be tethered to the power source and pulse generator and restrain its movement with the intrinsic twitching of muscles, motion of various body parts, and different postures (e.g., between lying down and standing up) that cause the stimulating leads to move, cause undue stress, and/or de-tethering. The very high difference between the elasticity of human tissue and the constrained electrode lead(s) can also cause addition scaring.

As a result, there is a need for improved devices, systems, and methods for electrically stimulating nerves and/or monitoring nerve activity.

SUMMARY

The present disclosure relates to neuromodulation and, more particularly, to devices, systems, and methods for electrically stimulating nerve(s), blocking nerve signaling, and/or monitoring nerve activity.

Aspects of the present disclosure utilize optical transmission of power and data to allow extremely small neuromodulation implants (e.g., 1 mm$^3$ and smaller in some instances) to be placed anywhere in the body (spinal cord, deep brain, vagus nerves, renal nerves, peripheral nerves, etc.) for use in electrical stimulation, blocking nerve signals, and/or recording nerve signals. For example, a multimode optical fiber implanted along with the neuromodulation implant can be utilized to transmit both high bandwidth information (e.g., a complex stimulation pattern) and power to the neuromodulation implant. In that regard, optical transceivers on each end of the multimode optical fiber (i.e., one at the end adjacent to the neuromodulation implant and one at the opposing end) facilitate communication of the high bandwidth information and/or power. Because such optical communications have essentially no signal loss in distances even in excess of 500 m, there is essentially no signal degradation in the much shorter distances associated with implanting a neuromodulation implant in a patient, regardless of where the neuromodulation implant is positioned within the body. In some implementations, the optical power and/or data transmissions can be performed directly, without use of an optical fiber. In this regard, due to the penetration of IR through tissue, bone, muscle, and body fluids, the optical power and/or data transmissions can, in some instances, be accomplished without the use of an optical fiber. The properties or parameters of the IR power source (e.g., an external laser) can be selected to ensure that the power and/or data transmissions reach a desired depth within the body to account for attenuation/losses related to the thickness and material makeup of the medium through which the signals will be transmitted.

The small size and ability to include a dense electrode array on the neuromodulation implants of the present disclosure facilitate precisely targeted electrical stimulation, blocking, and/or monitoring/recording. As a result, the devices, systems, and methods of the present disclosure can provide a better understanding of the anatomy and physiology of the neural circuits. For example, by measuring the physiological responses associated with particular therapeutic actions, the most effective stimulation parameters for a particular patient can be determined or identified (even after implantation). In that regard, the system allows complete flexibility in modifying the stimulation parameters after implantation. Further, by using the electrodes of the neuromodulation implant(s) to both provide stimulation or blocking and then measure the physiological responses, a closed loop control of optimized stimulation or blocking parameters can be implemented. Also, the off-target effects of neuromodulation can be minimized or eliminated.

The small size of the neuromodulation implants can also eliminate the need for traditional surgical procedures. For example, the neuromodulation implant (along with the optical fiber) can be implanted using a minimally invasive delivery syringe, cannula tube, or catheter as in injected versus being surgically implanted. This simple procedure can be performed without surgery (even outpatient surgery) and, therefore, is particularly suitable for use in emergency and/or combat situations. Further, the small size of the neuromodulation implants and limited impact of the implantation procedure minimizes adverse tissue response (e.g., scarring), minimizes discomfort, eliminates post-surgery complications and medical costs, and minimizes or eliminates the need for special surgical training. The injectable nature and small form factor also allows multiple implants even on the same nerve track or on different nerves.

The small size, the high bandwidth of optical communication, the use of application specific integrated circuits (ASICs), and the ability to include a small and/or dense electrode array on the neuromodulation implants of the present disclosure also allows for a high temporal and/or spatial resolution of stimulating and/or monitoring large nerve bundles. In that regard, the neuromodulation implants can combine neural stimulation, neural blocking (e.g., stimulation with AC signals around 50 KHz), and recording/monitoring or electrical signals on the same implant. In that regard, the neuromodulation implant can be provided as an implant on a single chip having a very small footprint (e.g., 0.5 mm$^2$ or less in some instances). Further, the neuromodulation implant can be encapsulated by a biocompatible glass or sapphire that is transparent to the specific laser used in order to protect the components from the harsh environment of the body. Because the neuromodulation implants rely on optical communication for transfer of both data and power, the resulting system is robust and reliable as it does not require electrical interconnects, wire bundles, connections to external assemblies, etc. Also, in accordance with the present disclosure, the neuromodulation implants can communicate with external devices without the need for a wired connection and without limiting where the neuromodulation implant can be positioned within the body. Because the neuromodulation implants of the present disclosure do not rely upon a battery, there is no concern of battery failure or the need to perform a subsequent surgery to replace/fix a battery for the neuromodulation implant to continue functioning.

Further, multiple neuromodulation implants can be implanted. In some instances, the stimulation parameters of the multiple neuromodulation implants can be coordinated. In this manner, a system of neuromodulation implants can provide coordinated stimulation to multiple nerves or nerve bundles and/or portions of a single nerve or nerve bundle. In this manner, the neuromodulation implants of the present disclosure allow for a modular neuromodulation system to be built up, where the neuromodulation implants can operate individually, coordinated, and/or combinations thereof. For example, multiple implants can be implanted on the same nerve or nerve bundle and one or more implants can be used to stimulate, while one or more other implants can be used to record the physiological reaction.

In an aspect of the disclosure, a neuromodulation system is provided. The neuromodulation system comprises: an implantable neuromodulation module in communication with an optical fiber, the implantable neuromodulation module including: a photodiode in optical communication with the optical fiber, the photodiode configured to receive light from the optical fiber and generate electrical power in response to receiving the light from the optical fiber; an optical transceiver in optical communication with the optical fiber, the optical transceiver configured to receive data from the optical fiber and transmit data to the optical fiber; and at least one electrode configured to provide electrical stimulation, blocking, or recording of a nerve utilizing the electrical power generated by the photodiode.

The neuromodulation system can include the optical fiber. In some instances, the optical fiber is a multi-mode optical fiber. The optical fiber is mechanically coupled to the implantable neuromodulation module in some implementations. In other instances, the optical fiber is not mechanically coupled to the implantable neuromodulation module such that it is spaced from and independently positionable relative to the implantable neuromodulation module. The light received by the photodiode from the optical fiber to generate the electrical current can be at a first wavelength and the data received by the optical transceiver from the optical fiber can be at a second wavelength, the second wavelength being different than the first wavelength. An optical filter can be positioned between the photodiode and the optical transceiver such that each receives the appropriate wavelength(s).

The neuromodulation system can further include an implantable relay module. The implantable relay module can include a radio frequency transceiver configured to communicate with a communications device outside of a patient body; and an optical transceiver in optical communication with the implantable module via the optical fiber. The implantable relay module can also include an infrared light source. In that regard, the optical transceiver of the implantable relay module can include the infrared light source. The optical transceiver of the implantable relay module can also include a light source separate from the infrared light source. The communication device can be a handheld computing device, a laptop computer, a desktop computer, or other suitable device. The signal path to the communication device could include a small wearable unit positioned close to or on the skin that transmits power and information to the relay module inside the body and may receive information from the relay module inside the body. The wearable unit can be powered with batteries or some other source. The wearable unit can communicate with a more sophisticated control unit such as a computer or mobile computer via Bluetooth or other communication channel.

The implantable neuromodulation module can also include a temporary power storage unit for storing the electrical power generated by the photodiode. In some instances, the temporary power storage unit includes a capacitor. The implantable neuromodulation module can also include a processing unit configured to process the data received by the optical transceiver. For example, the data received by the processing unit can include a stimulation profile and the processing unit can be further configured to selectively activate the electrode(s) based on the received stimulation profile. In that regard, the stimulation profile can include a spatial stimulation pattern and/or a temporal stimulation pattern.

The electrode(s) of the implantable neuromodulation module can include a penetrating electrode and/or a surface electrode. In some instances, the electrode(s) are self-imbedding such that a tack or other fixation device is not needed to maintain the implantable neuromodulation module in place within the body. In some implementations, the electrodes are part of a flexible electrode array. In some instances, a plurality of electrodes of varying profiles are provided. Further, in some instances the electrode(s) include a plurality of discrete stimulation and/or monitoring sites.

In an additional aspect of the disclosure, a method of neuromodulation is provided. The method comprises receiving, at a photodiode of a module positioned within a patient, light from an optical fiber and generating electrical current in response to receiving the light from the optical fiber; and providing, via at least one electrode of the module positioned within the patient, electrical stimulation to a nerve of the patient utilizing the electrical current generated by the photodiode.

In some instances, providing the electrical stimulation to the nerve includes selectively activating the electrode(s) in accordance with a stimulation profile. The stimulation profile can include a spatial stimulation pattern and/or a temporal stimulation pattern. In some implementations, the stimulation pattern is communicated from an external device to the module positioned within the patient via the optical fiber. In some instances, the method also includes monitoring an electrical pattern of the nerve with the at least one electrode of the module positioned within the patient and communicating the electrical pattern of the nerve to the external device via the optical fiber. In that regard, communicating the electrical pattern of the nerve to the external device can include wireless communication. For example, the wireless communication can be between a relay positioned within the patient and the external device, where the relay is in optical communication with module positioned within the patient via the optical fiber. At least one electrode can include a penetrating electrode positioned at least partially within the nerve and/or a surface electrode positioned adjacent to an external surface of the nerve. Further, in some instances the at least one electrode includes a plurality of discrete stimulation sites. In such instances, providing the electrical stimulation to the nerve can include selectively activating the discrete simulation sites.

Additional aspects, features, and advantages of the present disclosure will become apparent from the following detailed description.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details. In some instances, well-known structures and components are shown in block diagram form in order to avoid obscuring such concepts.

Figure 1:
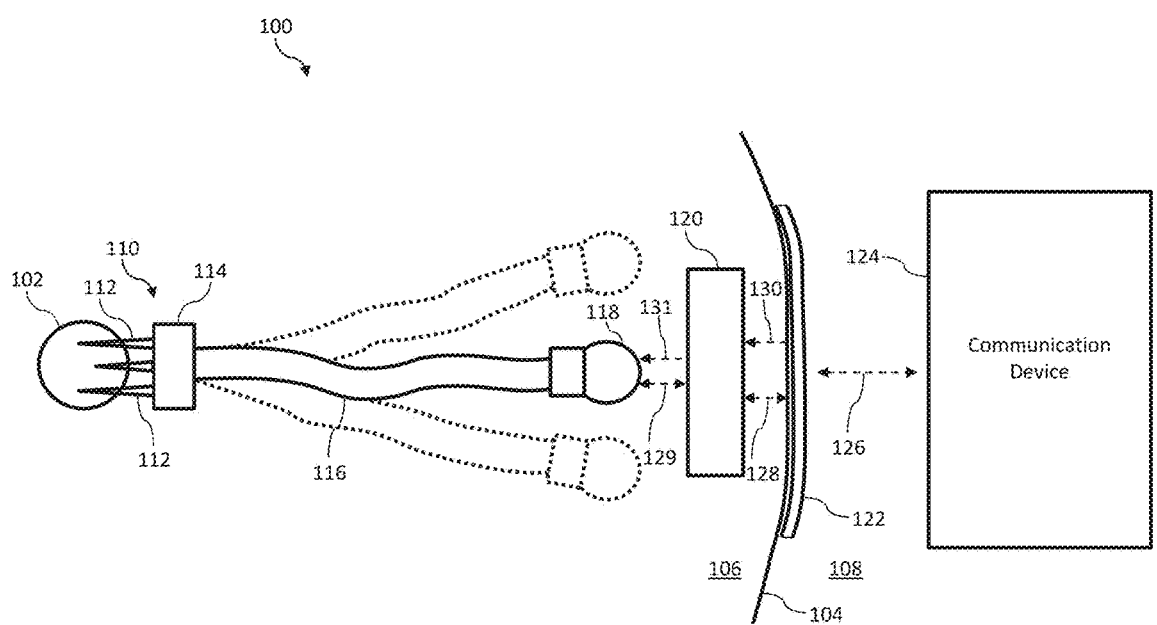
FIG. 1 is a diagram of an exemplary neuromodulation system according to embodiments of the present disclosure.

FIG. 1 is a diagram of an exemplary neuromodulation system 100 according to embodiments of the present disclosure. The neuromodulation system 100 is utilized to stimulate and/or monitor a nerve 102 of a patient. Generally, the nerve 102 is representative of a nerve or nerve bundle in any portion of the body, including spinal cord, deep brain, vagus nerves, renal nerves, peripheral nerves, etc. In that regard, a skin layer 104 is illustrated to distinguish between an area 106 inside the patient and an area 108 outside of the patient. It is understood that the relative distance between the nerve 102 and the skin layer 104 can vary greatly depending upon the particular nerve or nerve bundle of the patient.

The neuromodulation system 100 includes an implantable neuromodulation module 110. The implantable neuromodulation module 110 includes a plurality of electrodes 112 and a housing 114. The housing 114 is formed of and/or encapsulated by a biocompatible material. The housing 114 can contain various components of the implantable neuromodulation module 110, such as an optical transceiver, photodiode, laser source, temporary power storage, etc. as discussed in greater detail below.

The implantable neuromodulation module 110 can include any number of electrodes 112, including 1, 2, 3, 4, 8, 12, 24, 32, 48, 64, or more, up to thousands of electrodes. The electrodes 112 can be arranged in a linear array, a two-dimensional array, or other suitable spatial distribution. The electrodes 112 can be of various type, including penetrating electrodes, self-embedding electrodes (e.g., electrodes with a structural profile, such as an hourglass profile, that allows insertion into a nerve or nerve bundle, but resists or prevents unwanted removal without requiring a separate securing device, such as a tack), flat or surface electrodes, flexible electrodes, and/or combinations thereof. Further, in some instances each electrode may include a plurality of discrete stimulation and/or monitoring sites. In this regard, a penetrating electrode with a plurality of discrete stimulation and/or monitoring sites at various positions along the length of the electrode can be utilized to precisely target stimulation and/or monitoring at a desired depth or combination of different depths of the nerve 102. Similarly, by having an implantable neuromodulation module 110 with electrodes of different structural profiles (e.g., penetrating electrodes and surface electrodes, or different sizes of penetrating electrodes) stimulation and/or monitoring can be targeted to a desired depth or combination of different depths of the nerve 102.

The implantable neuromodulation module 110 is in communication with an optical fiber 116. The optical fiber 116 can be a multimode optical fiber. In this regard, the optical fiber 116 is configured to carry both power and data transmissions. In other instances, the optical fiber 116 can include two or more separate optical fibers, which may have dedicated purposes (e.g., power transmission to the implantable neuromodulation module 110, data transmission to the implantable neuromodulation module 110, data transmission from implantable neuromodulation module 110, etc.).

A lens 118 is coupled to the optical fiber 116. The lens 118 is configured to receive and/or focus light transmitted from an implantable relay 120. In this regard, the light transmitted from the implantable relay 120 can include power and/or data transmissions. The lens 118 can also be configured to transmit and/or focus light transmitted from the implantable neuromodulation module 110 onto the implantable relay. The light transmitted from the implantable neuromodulation module 110 can include data transmissions, such as neural activity monitoring performed by the implantable neuromodulation module 110. As shown in FIG. 1, the optical fiber 116 and the lens 118 are not fixed or anchored to the implantable relay 120. As a result, the optical fiber 116 and lens 118 may move around within the area 106 inside the body, but remain in general proximity of the implantable relay 120. Accordingly, the lens 118 is configured to receive and/or focus light from the implantable relay 120 and/or transmit and/or focus light to the implantable relay 120 even when offset with respect to the implantable relay 120. This ability of the optical fiber 116 and lens 118 to move within the patient's body can help reduce inflammation and scarring and, thereby, increase patient comfort. In some implementations, a Corning OptiFocus™ Collimating Lensed Fiber is utilized to provide the optical fiber 116 and lens 118 in an integrated component. Because the losses in the optical fiber of the power and communication signals is so low, the location of the implantable relay 120 and external communication patch can be selected to be more convenient for the patient.

Further, by utilizing optical communications, the neuromodulation system 100 can provide very high bandwidth stimulation and recording from even thousands of electrodes. For example, to illustrate the available bandwidth of the system consider an exemplary case of an electrode array having one thousand electrodes. To address a single electrode out of the one thousand electrode array can require 10 bits, a range of stimulation or measurement amplitude could be 1 ppm and require 20 bits, and another 10 bits can be provided for overhead. Accordingly, if it is desired to stimulate and/or monitor at a 100 KHz rate, then the required bandwidth is approximately 4 MB/s for each electrode and, therefore, approximately 4 GB/s for a one thousand electrode array, which is easily achievable with fiber optic communications. These values are exemplary and should not be considered limiting. These exemplary values are simply provided to illustrate how the neuromodulation system 100 can precisely control the stimulation and/or monitoring with high reliability utilizing the optical communication pathways.

As shown, the implantable relay device 120 is positioned in the area 106 inside the body, but in close proximity to the skin layer 104. As a result of its location close to the skin layer, the implantable relay device 120 can communicate with devices in the area 108 outside of the body relatively easily using various wireless communication techniques. The implantable relay 120 is in communication with an external communication patch 122. In this regard, the patch 122 is configured to transfer both power and data to the implantable relay 120 wirelessly. In some instances, the power and/or data are transmitted using radiofrequency (RF) communication. When both power and data are transmitted using RF communication, the RF communications for the power and data may be at different wavelengths. In some instances, the power and/or data are transmitted using infrared (IR) communication. In some instances, the power and data are transmitted using different communication techniques (e.g., RF communication for one and infrared (IR) communication for the other).

The external communication patch 122 facilitates communication between the implantable relay 120 and an external communication device 124. In this regard, the communication device 124 can be configured to provide stimulation profiles/patterns to the implantable neuromodulation module 110, process data received from the implantable neuromodulation module 110, and/or combinations thereof. The communication device 124 may be a mobile communication device (e.g., a smartphone, a cellular telephone, a personal digital assistant, etc.), a tablet computing device, a laptop computing device, a vehicle, a gaming console, a machine, a personal computing device, an e-reader device, a sensor device, another electronic device, or a combination of these devices, to name a few examples, that is operable to perform the operations described herein with respect to the communication device 124.

The communication device 124 may include a processor, a memory, a transceiver, and an antenna. These elements may be in direct or indirect communication with each other, for example via one or more buses. The processor of the communication device 124 may include a CPU, a DSP, an ASIC, a controller, a FPGA device, another hardware device, a firmware device, or any combination thereof configured to perform the operations described herein with reference to the communication device 124. The processor may also be implemented as a combination of computing devices, e.g., a combination of a DSP and a microprocessor, a plurality of microprocessors, one or more microprocessors in conjunction with a DSP core, or any other such configuration.

The memory of the communication device 124 may include a cache memory (e.g., a cache memory of the processor), RAM, MRAM, ROM, PROM, EPROM, EEPROM, flash memory, a solid state memory device, one or more hard disk drives, other forms of volatile and non-volatile memory, or a combination of different types of memory. In an embodiment, the memory includes a non-transitory computer readable medium. The memory may store instructions. The instructions may include instructions that, when executed by the processor, cause the processor to perform the operations described herein with reference to the communication device 124 in connection with embodiments of the present disclosure. Instructions may also be referred to as code, which may be interpreted broadly to include any type of computer-readable statement(s).

The transceiver of the communication device 124 may include a modem subsystem and a radio frequency (RF) unit. The transceiver is configured to communicate bi-directionally with other devices, such as patch 122 and/or implantable relay device 120. The modem subsystem may be configured to modulate and/or encode data. The RF unit may be configured to process (e.g., perform analog to digital conversion or digital to analog conversion, etc.) modulated/encoded data from the modem subsystem (on outbound transmissions) or of transmissions originating from another source such as patch 122 and/or implantable relay device 120. The modem subsystem and the RF unit may be integrated or separate devices that are coupled together at the communication device 124 to communicate with other devices.

The RF unit may provide the modulated and/or processed data, e.g. data messages, to the antenna for transmission to one or more other devices such as patch 122 and/or implantable relay device 120. After the transceiver receives a data message for transmission, the modem subsystem may modulate and/or encode the data message in preparation for transmission. The RF unit may receive the modulated and/or encoded data message and process the data message prior to passing it on to the antenna. The antenna may further receive data messages transmitted from patch 122 and/or implantable relay device 120, and provide the received data packets for processing and/or demodulation at the transceiver. The antenna may be a single antenna or include multiple antennas of similar or different designs in order to sustain multiple transmission links. Accordingly, in some implementations the communication device 124 can communicate with the patch 122 and/or implantable relay device 120 using a specific radio protocol and on a channel associated with the patch 122 and/or implantable relay device 120 (e.g., WLAN, Bluetooth, ZigBee, WiFi, etc.).

It is understood that the implantable relay device 120 and/or the patch 122 may include similar components to those described above with respect to communication device 124 (e.g., a processor, a memory, a transceiver, an antenna, etc.) to facilitate communication between the implantable relay device 120, the patch 122, and/or the communication device 124. However, for sake of brevity an expanded description will not be repeated for each of the implantable relay device 120 and the patch 122.

Figure 2:
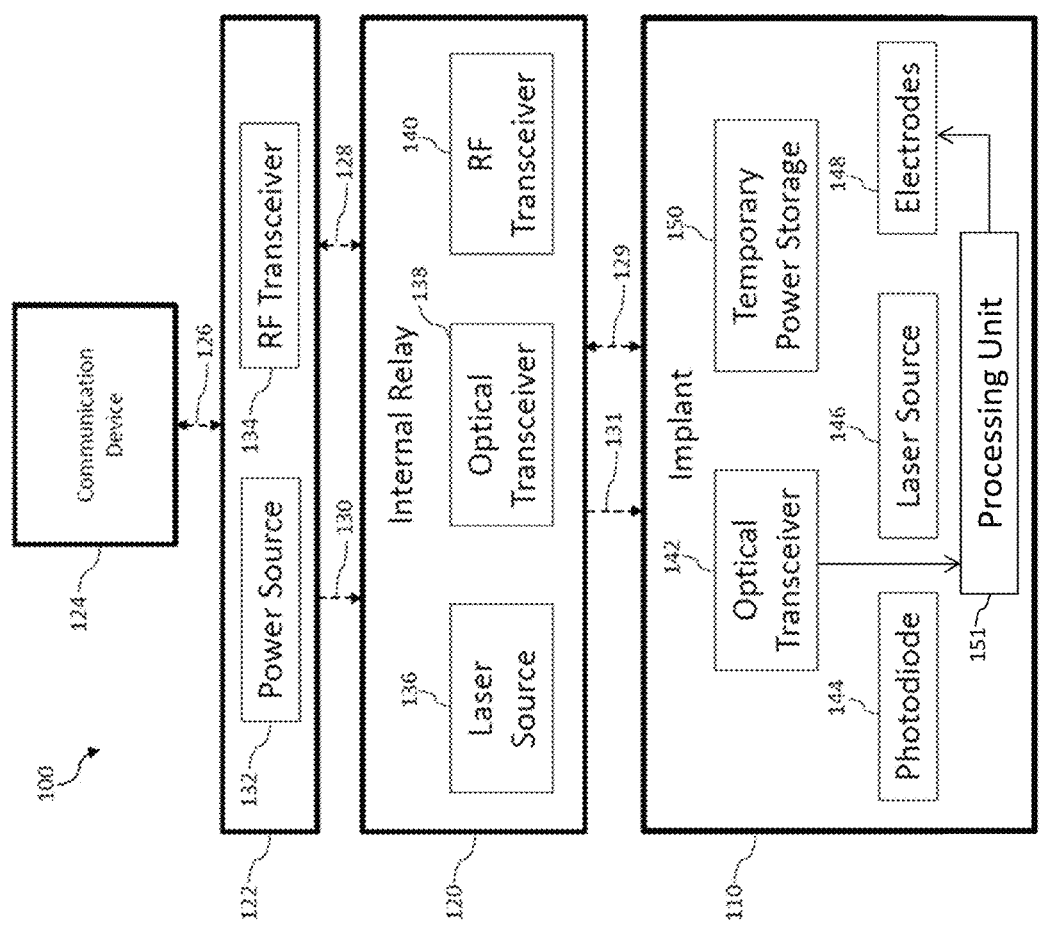
FIG. 2 is a schematic of an exemplary neuromodulation system according to embodiments of the present disclosure.

Referring now to FIG. 2, shown therein is a schematic of an exemplary neuromodulation system 100 according to embodiments of the present disclosure. In this regard, FIG. 2 illustrates additional aspects of the components of the implantable neuromodulation system 100 discussed above with respect to FIG. 1. The various communications between the components of the implantable neuromodulation system 100 described below can be seen in the context of both FIGS. 1 and 2.

As shown, the communication device 124 and the patch 122 have bidirectional communication as indicated by arrow 126. In that regard, communication 126 between the communication device 124 and the patch 122 can include transfer of data from the communication device 124 that is intended for the implantable neuromodulation module 110. For example, the communication device 124 may send one or more stimulation profiles that include spatial patterning, temporal patterning, strength of electrical stimulation, and/or combinations thereof.

The communication 126 between the patch 122 and the communication device 124 can also include transfer of data from the implantable neuromodulation module 110 to the communication device 124. For example, the implantable neuromodulation module 110 may send monitoring data representing the neural activity of the nerve 102 to the communication device 124 for processing and/or analysis. In some instances, the monitoring data can be utilized by the communication device 124 and/or a user (e.g., patient or medical personnel) of the communication device 124 to determine an appropriate stimulation profile. In some instances, the communication device 124 may store the data received from the implantable neuromodulation module 110 for later review and/or analysis. Further, in some instances, the communication device 124 may transfer the data received from the implantable neuromodulation module 110 on to a remote device, such as a computing device at a medical facility. In this regard, medical personnel at the medical facility may utilize the data to evaluate the effectiveness of the neuromodulation stimulation profiles and/or update the stimulation profiles to improve effectiveness.

Bidirectional communication between the patch 122 and the implantable relay 120, as indicated by arrow 128, and bidirectional communication between the implantable relay 120 and the implantable neuromodulation module 110 via optical fiber 116, as indicated by arrow 129, may facilitate communication of the data described above between the implantable neuromodulation module 110 and the communications device 124.

Further, the patch 122 may wirelessly transmit power to the implantable relay 120, as indicated by arrow 130. In this regard, the patch 122 may transmit an RF signal that is received by a coil(s) of the internal relay and utilized to power operation of the internal relay. Alternatively, the patch 122 may transmit an IR signal that is received by a photodiode or other suitable photovoltaic power converter, such that the received IR signal is converted into an electrical signal and utilized to power operation of the internal relay 120. The internal relay 120 may include one or more power storage components, such as a battery, capacitor, or otherwise for storing the power generated from the RF signals and/or IR signals.

Further, the internal relay 120 may transmit power to the implantable neuromodulation module 110 via optical fiber 116, as indicated by arrow 131. In this manner, both data 129 and power 131 can be transmitted to the implantable neuromodulation module 110 via the optical fiber 116. In this regard, it is understood that data and power may be transmitted to the implantable neuromodulation module 110 simultaneously over optical fiber 116. For example, power may be transmitted at one wavelength (or range of wavelengths), while data is transmitted at another wavelength (or range of wavelengths). Similarly, power may be transmitted over one or more fibers of the optical fiber 116, while data is transmitted over different fiber(s). The implantable neuromodulation module 110 may include one or more optical filters to filter the power and/or data such that the appropriate wavelength(s) is received at the corresponding receiver(s) of the implantable neuromodulation module 110. If IR rather than RF is used by patch 122 to send power and communications to and receive communications from the implantable unit 110, then the internal relay 120 may be omitted or simply be the passive lens 118 that collects and transmits power and communications from the patch 122 and transmits IR with communications to the patch 122.

Referring more specifically to FIG. 2, additional aspects of the components of the neuromodulation system 100 are shown. As mentioned above, it is understood that the components may have various other components, such as power supplies, processors, amplifiers, filters, memory, antennas, etc., to facilitate the operations described herein that are not explicitly shown in FIG. 2. As a result, the following description focuses on only certain aspects of the components for sake of clarity and brevity. As shown, the patch 122 includes a power source 132 and an RF transceiver 134. In this regard, the power source 132 is configured to wirelessly transmit a power signal to the implantable relay 120. As discussed above, the power signal can include an RF power signal, an IR power signal, other suitable wireless signal, and/or combinations of such signals that are receivable by the implantable relay 120 and that can be converted into energy for use in operating the implantable relay.

The RF transceiver 134 of the patch 122 can include one or multiple transceivers. In that regard, the RF transceiver 134 is configured to facilitate RF communication with the communication device 124 and the internal relay 120. The RF communications with the communication device 124 may operate at a different frequency and/or using a different protocol than the RF communications with the internal relay 120. Accordingly, in some implementations separate RF transceivers are provided for communication with the communication device 124 and the internal relay 120.

Figure 7:
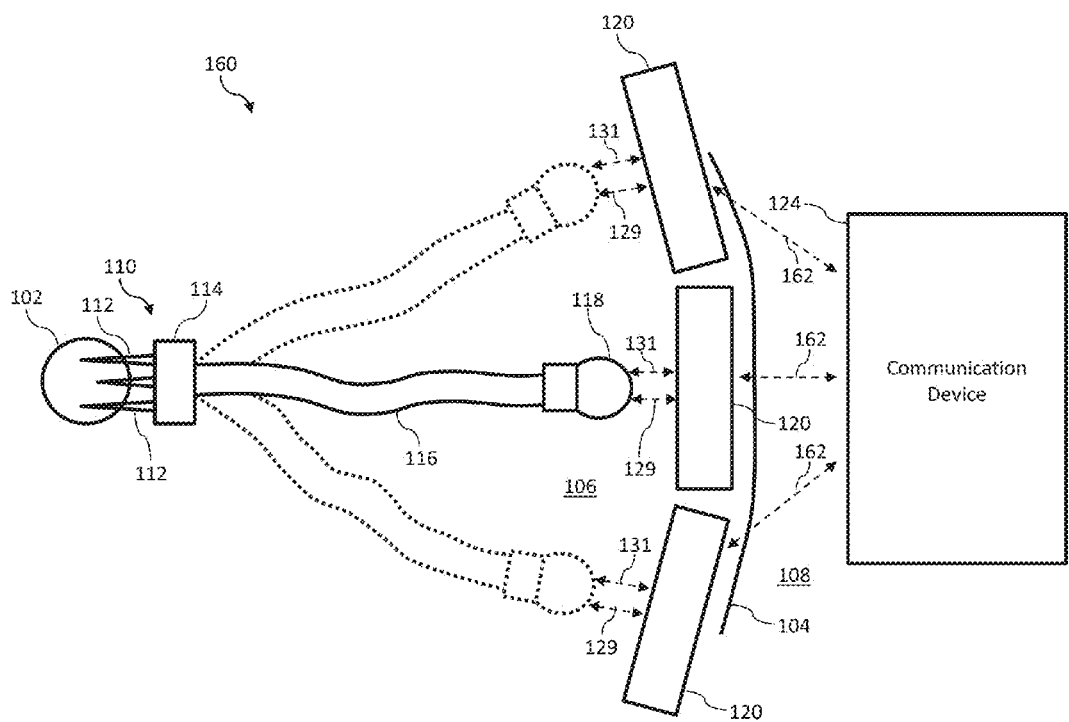
FIG. 7 is a diagram of an exemplary neuromodulation system according to embodiments of the present disclosure.

As shown in FIG. 2, the internal relay 120 can include a laser source 136, an optical transceiver 138, and an RF transceiver 140. The RF transceiver 140 of the internal relay 120 can include one or multiple transceivers. In that regard, the RF transceiver 140 can be configured to facilitate RF communication with the patch 122 and/or the communication device 124. In that regard, as shown in the implementation of FIG. 7, the internal relay 120 is configured to communicate directly with the communication device 124 in some instances. The RF communications with the communication device 124 may operate at a different frequency and/or using a different protocol than the RF communications with the patch 122. Accordingly, in some implementations the RF transceiver 140 includes separate transceivers for communication with each of the patch 122 and the communication device 124.

The laser source 136 is configured to transmit light towards the lens 118 such that the associated signals can be transmitted along the optical fiber 116 to the implantable neuromodulation module 110. In this regard, in some instances the laser source 136 is configured to transmit a power signal to the implantable neuromodulation module 110. For example, in some instances the power signal is an IR signal. In other instances, the power signal has a wavelength outside of the IR range.

The optical transceiver 138 of the internal relay 120 is configured to facilitate communication of optical data with the implantable neuromodulation module 110. In that regard, the optical transceiver 138 can include a multiplexer(s), a de-multiplexer(s), a photodetector(s), a light source(s), a modulator(s), a de-modulator(s), and/or other suitable components. In some instances, the optical transceiver 138 is configured to transmit data (e.g., stimulation profiles) received by the internal relay 120 from the patch 122 and/or communication device 124 via the RF transceiver 140 to the implantable neuromodulation module 110 in optical form. Likewise, the optical transceiver is configured to receive data transmitted from the implantable neuromodulation module 110 (e.g., neural monitoring data) in optical form that is subsequently transmitted to the patch 122 and/or communication device 124 utilizing RF transceiver 140. While the laser source 136 and the optical transceiver 138 are depicted as separate components, in some instances the laser source 136 is part of the optical transceiver 138. For example, the laser source 136 can be a light source of the optical transceiver 138. As a result, in some implementations the functions of the laser source 136 and the optical transceiver 138 are performed by an integrated component. As discussed below, FIGS. 3-6 illustrate aspects of optical transceiver arrangements suitable for use as the optical transceiver 138.

As shown in FIG. 2, the implantable neuromodulation module 110 can include an optical transceiver 142, a photodiode 144, laser source 146, electrodes 148, and temporary power storage 150. The optical transceiver 142 of the implantable neuromodulation module 110 is configured to facilitate communication of optical data with the internal relay 120. In that regard, the optical transceiver 142 can include a multiplexer(s), a de-multiplexer(s), a photodetector(s), a light source(s), a modulator(s), a de-modulator(s), and/or other suitable components. In some instances, the optical transceiver 142 is configured to receive data (e.g., stimulation profiles) transmitted by the internal relay 120 as relayed from the patch 122 and/or communication device 124. Likewise, the optical transceiver 142 is configured to transmit data (e.g., neural monitoring data) to the internal relay via optical fiber 116. In that regard, the implantable neuromodulation module 110 may utilize the laser source 146 to transmit data to the internal relay 120.

Figure 13:
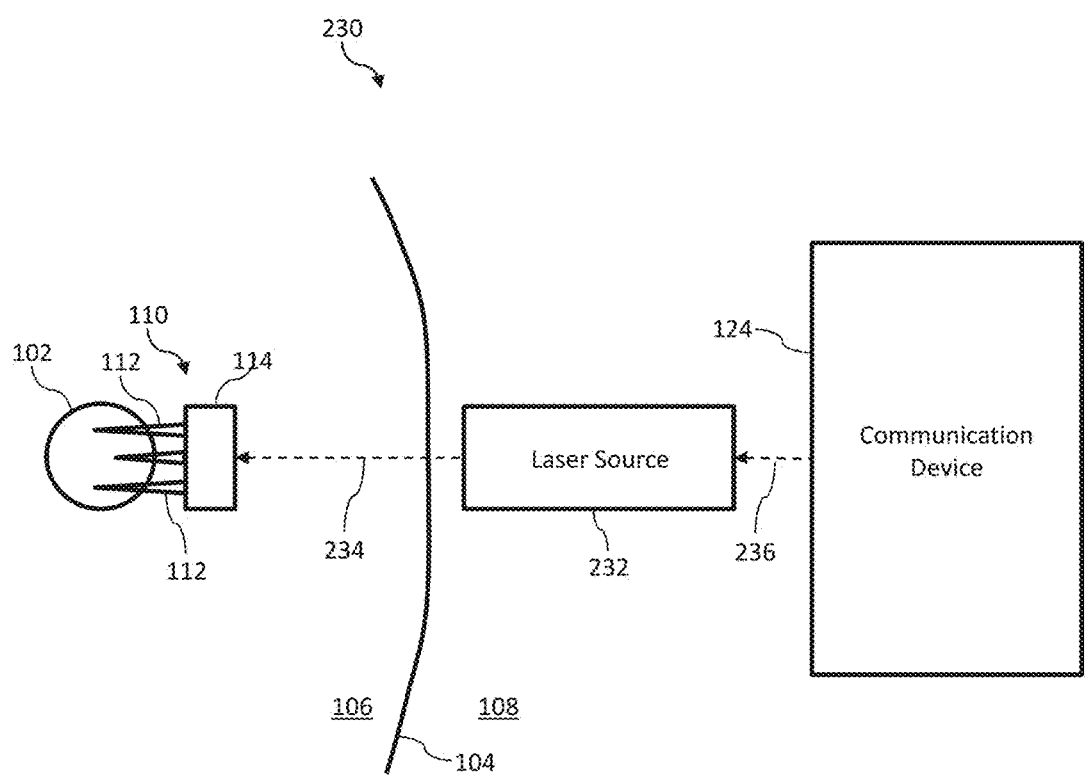
FIG. 13 is a diagram of an exemplary neuromodulation system according to embodiments of the present disclosure.

The photodiode 144 of the implantable neuromodulation device 110 is configured to receive light and convert the received light into an electrical signal. Generally, the photodiode 144 may be any suitable photovoltaic power converter. In the illustrated embodiment, the photodiode 144 is configured to receive light from the laser source 136 of the internal relay 120 via the optical fiber 116. However, in other implementations the photodiode 144 can be configured to receive light directly from a light source positioned outside of the patient's body, as shown in FIG. 13.

While the optical transceiver 142, photodiode 144, and the laser source 146 are depicted as separate components, in some instances the photodiode 144 and/or the laser source 146 is part of the optical transceiver 142. For example, the laser source 146 can be a light source of the optical transceiver 142. As a result, in some implementations the functions of the optical transceiver 142, the photodiode 144, and/or the laser source 146 are performed by an integrated component. As discussed below, FIGS. 3-6 illustrate aspects of optical transceiver arrangements suitable for use as the optical transceiver 142. In that regard, the arrangements of FIGS. 4-6 illustrate a component having an integrated optical transceiver, photodiode, and laser source.

In some implementations, the laser source 146 is configured to provide optical stimulation to the nerve 102. In this regard, the laser source 146 can be separate from the laser source(s) utilized for data communications. For example, the laser source 146 can provide a stimulation beam having a different wavelength(s) than the data communication wavelength(s). Further, the laser source 146 can include multiple laser sources, having the same or different properties, for providing the optical stimulation to the nerve. In this regard, the optical stimulation can be provided using stimulation profiles with variable spatial and/or temporal patterning by selectively activating the different laser sources and/or controlling one or more parameters of the optical stimulation beam produced by the laser sources. Accordingly, in some implementations the implantable neuromodulation module 110 is configured to provide both electrical stimulation and optical stimulation to the nerve 102. Further, in some implementations a stimulation profile combines and coordinates the electrical and optical stimulations spatially and/or temporally.

The implantable neuromodulation module 110 can also include a processing unit 151 configured to process the data received by the optical transceiver 142. For example, the data received by the processing unit 151 can include a stimulation profile and the processing unit 151 can be further configured to selectively activate the electrode(s) 148 based on the received stimulation profile. In that regard, the stimulation profile can include a spatial stimulation pattern and/or a temporal stimulation pattern.

Figure 3:
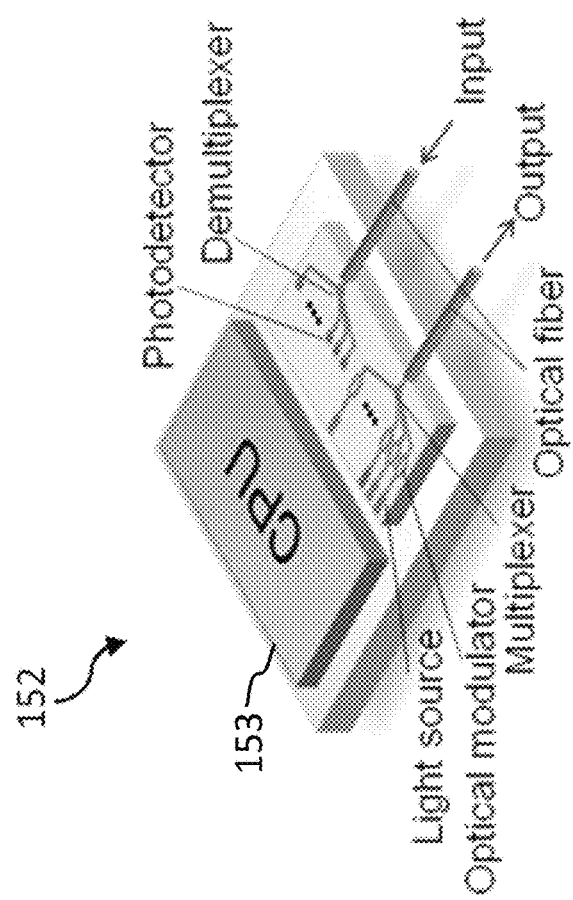
FIG. 3 is a perspective view of an exemplary transceiver according to embodiments of the present disclosure.
Figure 4:
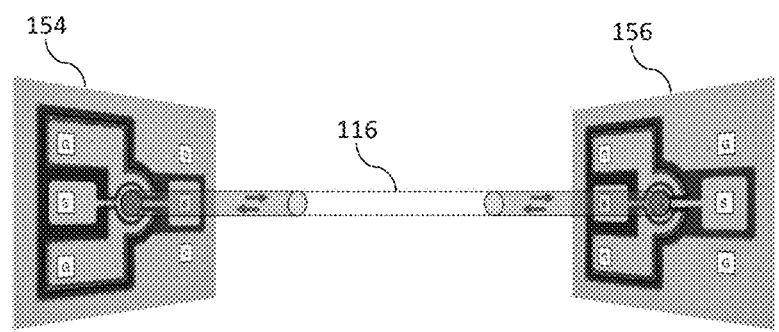
FIG. 4 is a perspective view of an exemplary arrangement of transceivers according to embodiments of the present disclosure.
Figure 5:
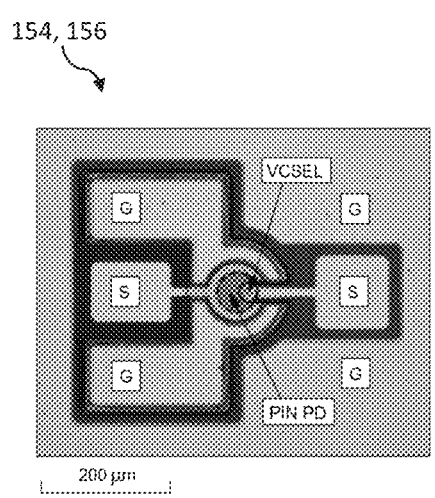
FIG. 5 is a top view of an exemplary transceiver according to embodiments of the present disclosure.
Figure 6:
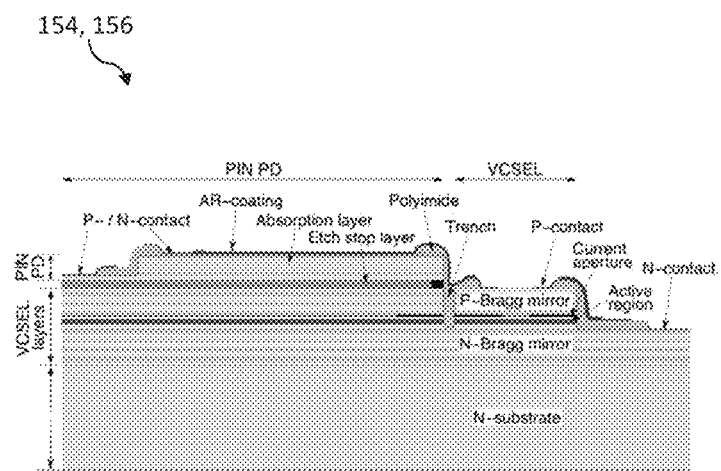
FIG. 6 is a cross-sectional side view of the exemplary transceiver of FIG. 5 according to embodiments of the present disclosure.

Referring now to FIGS. 3-6, shown therein are exemplary arrangements of optical transceivers for use with the neuromodulation systems of the present disclosure. Referring initially to FIG. 3, shown therein is a perspective view of an exemplary optical transceiver 152 according to embodiments of the present disclosure. As shown, the optical transceiver 152 includes an optical fiber input to a de-multiplexer and photodetector. The optical transceiver 152 also includes a light source, optical modulator, and multiplexer leading to an optical fiber output. In the illustrated embodiment, the optical fiber input and output are separate fibers, but in other implementations can be a single multi-mode optical fiber. The optical transceiver 152 also includes a processor (CPU) 153 to facilitate processing of data received via the optical fiber input, processing of data to be transmitted out via the optical fiber output, and/or execute instructions for operation of other aspects of the optical transceiver 152.

Referring now to FIGS. 4-6, another optical transceiver arrangement for use with the neuromodulation systems of the present disclosure is provided. In this regard, FIG. 4 is a perspective view of the exemplary arrangement of transceivers 154 and 156; FIG. 5 is a top view of an exemplary structure for transceiver 154, 156; and FIG. 6 is a cross-sectional side view of the structure of the transceiver 154, 156 of FIG. 5. As shown in FIG. 4, the optical transceivers 154 and 156 can be in optical communication with one another via optical fiber 116. In this regard, the optical transceivers 154 and 156 can serve as the optical transceivers of the internal relay 120 and the implantable neuromodulation module 110 in some instances. Accordingly, in some instances at least one of the optical transceivers 154, 156 will not be mechanically coupled to the optical fiber 116 as shown in FIG. 4. For example, in some instances at least one end of the optical fiber 116 will include a lens 118 that is positioned adjacent to or proximity of the optical transceiver 154, 156 but independently positionable relative to the optical transceiver 154, 156.

As best shown in FIGS. 5 and 6, the optical transceivers 154, 156 include a photodiode, such as a PIN diode, and a vertical-cavity surface-emitting laser (VCSEL) integrated into a single chip having a small footprint (e.g., less than about 0.5 mm$^2$, such as approximately 0.3 mm$^2$ as shown in the illustrated embodiment). FIG. 6 illustrates additional details of the chip construction of the optical transceivers 154, 156. As shown, the PIN diode of the optical transceivers 154, 156 is defined by a plurality of layers, including an anti-reflective coating, an absorption layer, and an etch stop layer. Further, as shown the VCSEL of the optical transceivers 154, 156 is defined by a plurality of layers, including P-Bragg mirror, a current aperture, an active region (e.g., including one or more quantum wells), an N-Bragg mirror, and an N substrate. Each of the PIN diode and VCSEL also include P-type and N-type contacts, as shown.

Referring now to FIG. 7, shown therein is a diagram of an exemplary neuromodulation system 160 according to embodiments of the present disclosure. In that regard, the neuromodulation system 160 is similar in many respects to the neuromodulation system 100 of FIGS. 1 and 2. However, as shown, the neuromodulation system 160 includes multiple internal relays 120 positioned within the body of the patient. Generally, any number of internal relays 120 can be utilized, including 1, 2, 3, 4, or more. In the illustrated embodiment the neuromodulation system 160 is shown having three separate internal relays 120. As shown, by having multiple internal relays 120 the allowable range of movement of the optical fiber 116 and lens 118 can be increased while maintaining the ability of the system to function. In particular, the lens 118 and optical fiber 116 can transmit and/or receive signals from the internal relay(s) 120 in closest proximity and/or alignment.

Further, in the illustrated embodiment of FIG. 7 the internal relays 120 are shown communicating directly with the communication device 124 (as indicated by arrows 162) instead of indirectly, through patch 122, as shown in FIGS. 1 and 2. In this regard, the communication device 124 can transmit data and/or power signals to the internal relays. The communication device 124 may simultaneously communicate with two or more internal relays 120 in some implementations. In other implementations, the communication device 124 communicates with a single internal relay 120 at a time. In some instances where multiple internal relays 120 are present within the patient, each of the internal relays 120 can be configured to provide feedback indicative of whether the internal relay 120 is able to communicate with the implantable neuromodulation module 110. In some instances, the feedback can be a response or acknowledgment signal transmitted from the implantable neuromodulation module 110 in response to a beacon or pilot signal transmitted by the communication device 124 and relayed by the internal relay 120. Accordingly, the communication device 124 can communicate with the different internal relays 120 until a connection with the implantable neuromodulation module 110 is established.

Figure 8:
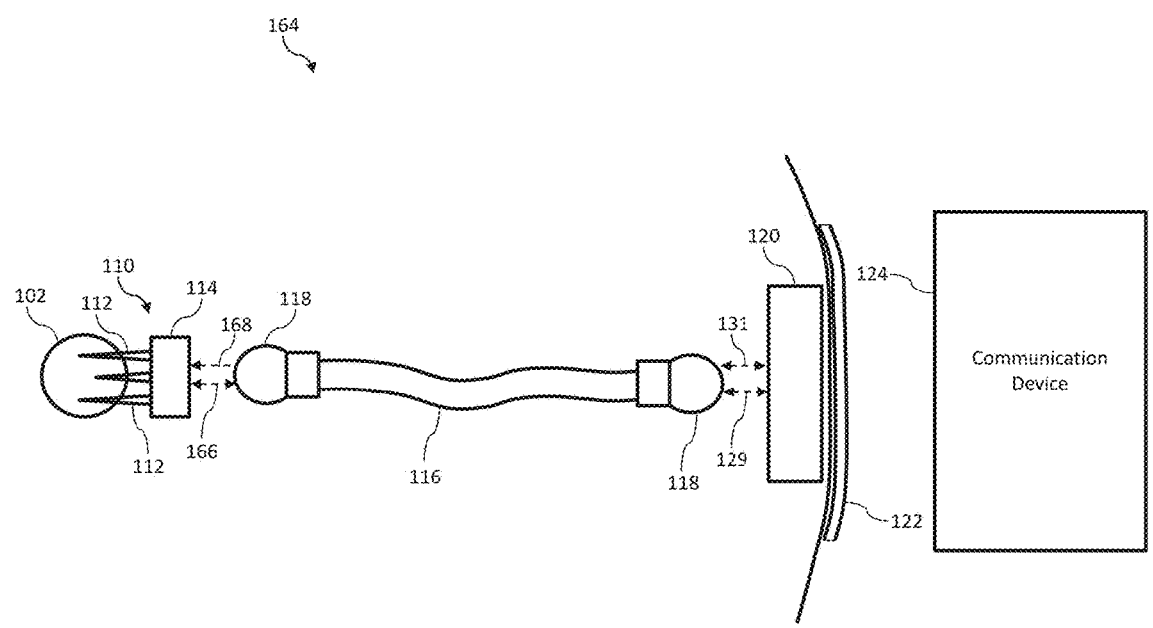
FIG. 8 is a diagram of an exemplary neuromodulation system according to embodiments of the present disclosure.

Referring now to FIG. 8, shown therein is a diagram of an exemplary neuromodulation system 164 according to embodiments of the present disclosure. In that regard, the neuromodulation system 164 is similar in many respects to the neuromodulation systems 100 and 160 of FIGS. 1, 2, and 7. However, in the neuromodulation system 164 of FIG. 8 the optical fiber 116 is not mechanically coupled to the implantable neuromodulation module 110. Instead, the end of the optical fiber 116 adjacent to the implantable neuromodulation module 110 also includes a lens 118 such that the optical fiber 116 includes lenses 118 at each end. Similar to the lens 118 adjacent to the internal relay 120, the lens 118 adjacent to the implantable neuromodulation module 110 is configured to receive and/or focus light transmitted from the implantable neuromodulation module 110 into the optical fiber 116 and/or transmit and/or focus light from the optical fiber 116 onto the implantable neuromodulation module 110. In this regard, the light transmitted and/or received by the lens 118 can include data transmissions 166 and/or power transmissions 168 to and/or from the implantable neuromodulation module 110, as described above. In some implementations, a Corning OptiFocus™ Collimating Lensed Fiber is utilized to provide the optical fiber 116 and lenses 118 in an integrated component.

Figure 9:
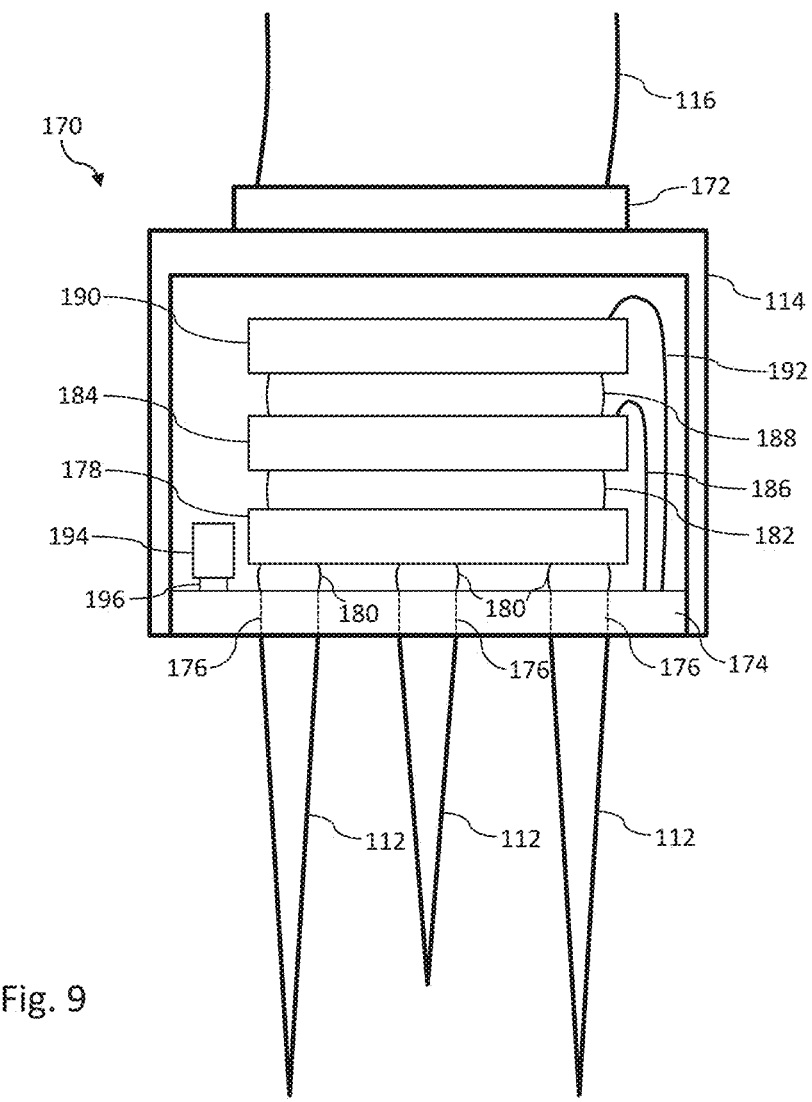
FIG. 9 is a diagrammatic, partial cross-sectional side view of an implantable neuromodulation module according to embodiments of the present disclosure.

Referring now to FIGS. 9-12, shown therein are exemplary arrangements of implantable neuromodulation modules for use with the neuromodulation systems of the present disclosure. Referring initially to FIG. 9, shown therein is a diagrammatic, partial cross-sectional side view of an implantable neuromodulation module 170 according to embodiments of the present disclosure. As shown, the implantable neuromodulation module 170 includes electrodes 112 and an encapsulating housing 114 as discussed above. In this regard, the electrodes can be formed of any suitable material, including without limitation glass, silicon, inert metals, nanocrystalline diamond, and/or combinations thereof. The encapsulating housing 114 can be formed of a suitable biocompatible material, including without limitation glass, sapphire, silicon, polymers, and/or combinations thereof. In some instances, the material used for the housing 114 is selected such that it is transparent to the wavelengths of light utilized to transmit power and/or data signals to the implantable neuromodulation module 170.

In the illustrated embodiment, a lens 172 is coupled to the housing 114. The lens 172 can function in a similar manner to the lens 118 adjacent to the implantable neuromodulation module as shown and described in the context of FIG. 8, but with a fixed orientation with respect to the implantable neuromodulation module 170. The lens 172 can be any suitable lens, including without limitation lensed fiber, glass and other biocompatible material lens, and/or combinations thereof. In some implementations, a Corning OptiFocus™ Collimating Lensed Fiber is utilized to provide the optical fiber and lens in an integrated component. In such instances, the lens can be secured to the housing 114 using an adhesive, epoxy, or other suitable material. In some instances, the lens 172 is positioned within the housing 114.

As shown in FIG. 9, the implantable neuromodulation module 170 has a chip-based architecture. To this end, a substrate 174 is provided. The substrate 174 can be formed of any suitable material, including without limitation silicon, glass, metal, polymers, and/or combinations thereof. Through vias 176 extend through the substrate 174 to the electrodes 112. In this regard, the vias 176 carry electrical signals to and from the electrodes for use in providing electrical stimulation and monitoring neural activity. The vias can be formed of any suitable conductive material, including without limitation copper, polysilicon, silicon, gold and other metals used in semiconductor processing and packaging, and/or combinations thereof.

A multiplexer/de-multiplexer chip 178 is flip-chip bonded to the substrate using solder 180. An epoxy layer 182 is positioned over the multiplexer/de-multiplexer chip 178 and secures an optical transceiver chip 184 in place. The epoxy layer 182 can be formed of a suitable material, including without limitation underfill epoxies, solder pastes using lead based solders and lead free solders, conductive and nonconductive epoxies, and/or combinations thereof. The optical transceiver chip 184 can include one or more optical filters. In some instances the optical filter(s) filter out light in wavelength ranges outside of the desired wavelength range for data communication. For example, the filter(s) can filter out the light utilized to power the implantable neuromodulation module 170 in some instances. Any suitable optical filters can be utilized, including without limitation thin film stacked high bandwidth filters, low bandwidth filters, and/or combinations thereof. In some instances, the material utilized for the epoxy layer 182 is selected to allow light within a particular wavelength range(s) to pass through to the multiplexer/de-multiplexer chip 178, such as the light filtered by the transceiver chip 184. As shown, the transceiver chip 184 can be wire bonded to the substrate 174 via a wire 186.

An epoxy layer 188 is positioned over the transceiver chip 184 and secures a photovoltaic power chip 190 in place. The epoxy layer 188 can be formed of a suitable material, including without limitation conductive or nonconductive epoxies and metal pastes, and/or combinations thereof. In some instances, the material utilized for the epoxy layer 188 is selected to allow light within a particular wavelength range(s) to pass through to the transceiver chip 184. Similarly, the photovoltaic power chip 190 can be transparent to light within particular wavelength range(s) to allow the light to pass through to the epoxy layer 188 and on to the transceiver chip 184. The photovoltaic power chip 190 can be any suitable type, including without limitation a photodiode, a PIN photodiode, VCSEL, and/or combinations thereof. The photovoltaic power chip 190 is configured to produce electrical current in response to receiving light. In some instances, the light received by the photovoltaic power chip 190 is transmitted along the length of the optical fiber 116 to the implantable neuromodulation module 170. In this regard, the optical fiber 116 may be mechanically coupled to the implantable neuromodulation module 170 (as shown in FIG. 9), either with or without lens 172. The optical fiber 116 can also be spaced from and independently moveable relative to the implantable neuromodulation module 170 (as shown in FIG. 8). In yet other instances, the light received by the photovoltaic power chip 190 is transmitted through portions of the body, without the use of an optical fiber. For example, when the implantable neuromodulation module 170 is implanted at a position relative shallow in the body such that it is close the skin layer 104, a device positioned outside of the body can transmit IR light directly to the photovoltaic power chip 190 without using an optical fiber (as shown in FIG. 13). As shown, the photovoltaic power chip 190 can be wire bonded to the substrate 174 via a wire 192. While the illustrated embodiment, shows the photovoltaic power chip 190, the optical transceiver chip 184, and the multiplexer/de-multiplexer chip 178 in a stacked arrangement, in other implementations one or more of these components can be mounted side by side or otherwise offset. In such side by side or offset arrangements, there is no need for the components to be transparent to the wavelength(s) of light utilized by the other components.

The implantable neuromodulation module 170 also includes one or more temporary power storage devices 194. The temporary power storage device 194 can be any suitable device, including without limitation a capacitor, thin film solid state battery, ultracapacitor, and/or combinations thereof. The temporary power storage device 194 can be configured to store the electrical energy generated by the photovoltaic power chip 190 for use by other components of the implantable neuromodulation module 170. For example, the energy stored in the temporary power storage device 194 can be utilized to activate the electrodes 112 during neurostimulation. In the illustrated embodiment, the temporary power storage device 194 is flip-chip bonded to the substrate 174 using solder 196.

Figure 10:
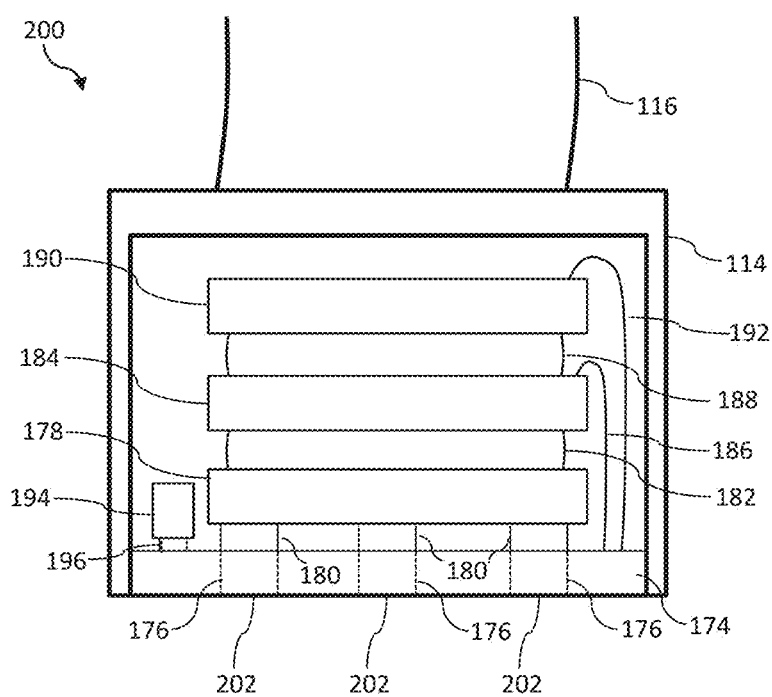
FIG. 10 is a diagrammatic, partial cross-sectional side view of an implantable neuromodulation module according to embodiments of the present disclosure.

Referring now to FIG. 10, shown therein is a diagrammatic, partial cross-sectional side view of an implantable neuromodulation module 200 according to embodiments of the present disclosure. In many respects, the implantable neuromodulation module 200 is similar to the implantable neuromodulation module 170 described above with respect to FIG. 9. However, the implantable neuromodulation module 200 does not utilize lens 172, instead the optical fiber 116 is coupled directly to the implantable neuromodulation module 200. Further, instead of penetrating electrodes 112, the implantable neuromodulation module 200 includes surface electrodes 202 that are defined by the through vias 176 extending through the substrate 174. As noted previously, it is understood that the implantable neuromodulation modules of the present disclosure can include any combination of electrode structure types (e.g., penetrating, self-embedding, surface, etc.) and in any type of pattern/array.

Figure 11:
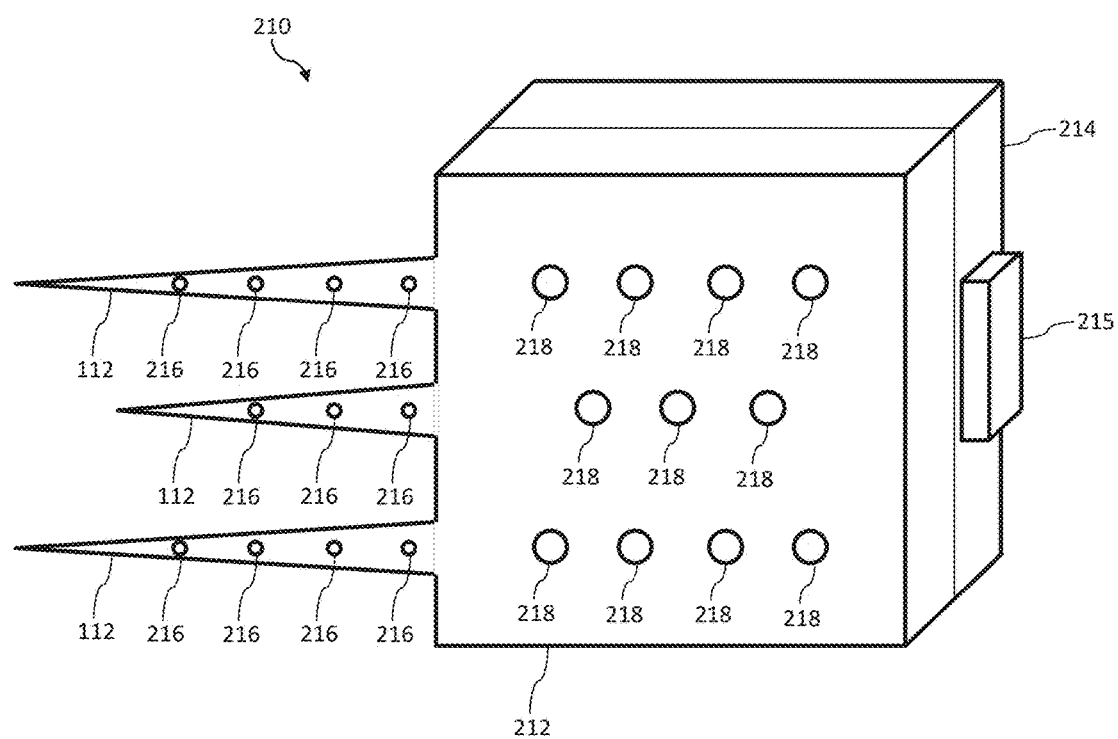
FIG. 11 is a diagrammatic perspective front side view of an implantable neuromodulation module according to embodiments of the present disclosure.
Figure 12:
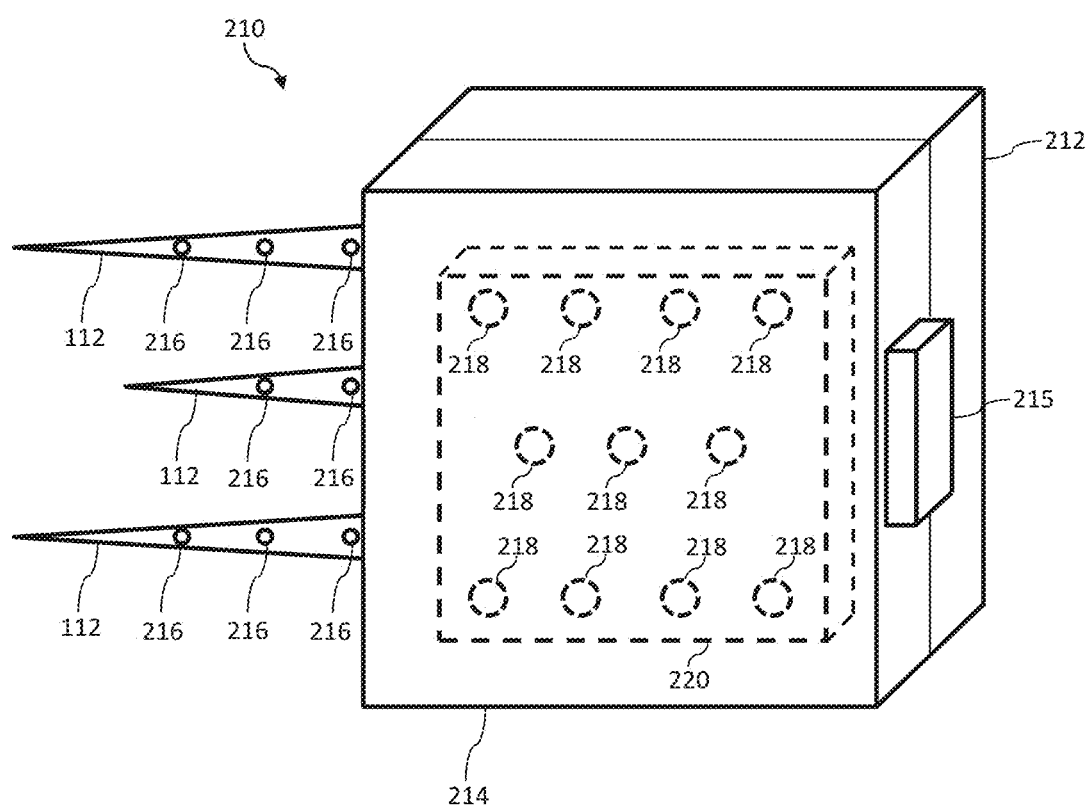
FIG. 12 is a diagrammatic perspective back side view of the implantable neuromodulation module of FIG. 11 according to embodiments of the present disclosure.

Referring now to FIGS. 11 and 12, shown therein are diagrammatic perspective front side and back side views, respectively, of an implantable neuromodulation module 210 according to embodiments of the present disclosure. The implantable neuromodulation module 210 can include features similar to the implantable neuromodulation modules 170 and 200 described above. For example, as shown, the implantable neuromodulation module 210 includes an encapsulating housing 212, a substrate 214, and a transceiver chip 220 (shown in FIG. 12). A lens 215 is mechanically coupled to the encapsulating housing 212. The lens 215 may also be mechanically coupled to an optical fiber in some implementations. Further, in some instances the lens 215 can be positioned inside of the housing 212. The implantable neuromodulation module 210 includes penetrating electrodes 112 that have a plurality of stimulation/monitoring sites 216. The implantable neuromodulation module 210 also includes through vias 218 that define surface electrodes.

As shown, the plurality of stimulation/monitoring sites 216 are spaced along the length of the electrodes. The plurality of stimulation/monitoring sites 216 can also be spaced about the circumference/perimeter of the electrodes. Similarly, the through vias 218 that define the surface electrodes are spaced about the substrate 214. By spacing the stimulation/monitoring sites 216 and/or the through vias 218, stimulation and/or monitoring can be performed at a desired location or combination of different locations of the nerve or nerve bundle. In this regard, in some instances the stimulation/monitoring sites 216 and/or the through vias 218 are individually addressable and/or activatable such that virtually any combination of spatial and/or temporal pattern of stimulation and/or monitoring can be implemented. In some instances, two or more of the stimulation/monitoring sites 216 and/or the through vias 218 are grouped such that they are activated together to provide simultaneous stimulation and/or monitoring. In order to allow for the discrete stimulation/monitoring sites 216 on the penetrating electrodes 112, the body of the penetrating electrodes can be formed from a suitable insulating material, including without limitation nonconductive oxides, silicon carbide, silicon nitride, silicon oxide, nano crystalline diamond, parylene C, nonconductive polymers, and/or combinations thereof, while the discrete stimulation/monitoring sites 216 are defined by a suitable conductive material, including without limitation titanium, titanium nitride (TiN), platinum, iridium, gold, nanocrystalline diamond, and/or combinations thereof.

Referring now to FIG. 13, shown therein is a diagram of an exemplary neuromodulation system 230 according to embodiments of the present disclosure. In that regard, the neuromodulation system 230 is similar in many respects to the neuromodulation systems 100, 160, and 164 of FIGS. 1, 2, 7, and 8. However, in the neuromodulation system 230 of FIG. 13, the implantable neuromodulation module 110 receives at least a power signal directly from a device outside of the body. In the illustrated embodiment, a laser source 232 positioned outside of the body transmits at least a power signal 234 to the implantable neuromodulation module 110. The laser source 232 is in communication with a communication device 124 as indicated by arrow 236. In this regard, the communication device 124 may control or send instructions to the laser source 232 as to when to send power to the implantable neuromodulation module 110. The communication 236 between the communication device 124 and laser source 232 can be wired or wireless. In some instances, the laser source 232 and the communication device 124 are part of a common or integrated device or system. The laser source 232 can also be contained within the patch 122. Further, in some instances the laser source 232 can include a plurality of laser sources.

The laser source 232 (or the communication device 124 in communication with the laser source 232) can adjust the power signal 234 to account for the location of the implantable neuromodulation module 110 within the patient. For example, the penetration of the power signal 234 can be adjusted by varying the power, wavelength, pulse profile (e.g., pulsed or continuous wave), etc. of the laser source 232 to account for the location of the implantable neuromodulation module 110, including the type(s) of medium (bone, tissue, nerve, bodily fluids, etc.) between the laser source and the implantable neuromodulation module 110. In some instances, the implantable neuromodulation module 110 makes data communications over an optical fiber 116 similar to the previously described embodiments. However, in some implementations the arrangement of FIG. 13 is particularly suited for the implantable neuromodulation module 110 to only provide stimulation and not monitoring, thereby eliminating the need for two-way communication.

In this regard, power signal 234 received from the laser source 232 can be sufficient to drive the stimulation pulses of the electrodes 112 of the implantable neuromodulation module 110 in accordance with a stimulation profile. In that regard, the stimulation profile may be predefined for the implantable neuromodulation module 110 such that the implantable neuromodulation module 110 executes the same stimulation profile over time. In other instances, the stimulation profile can be updated from time to time. For example, in some instances the implantable neuromodulation module 110 includes rewriteable memory that stores the stimulation profile such that the memory can be updated wirelessly, as needed, to update the stimulation profile.

As shown in FIG. 13, in some implementations the implanted relay 120 can be omitted and all power and communications happen between the lens 118 and the patch 122 or other external device via infrared. The position of the patch 122 or other external device can be adjusted until a good coupling with lens is achieved. Further, in some instances, multiple laser transceivers could be used spread into an array, within a single patch/device or by utilizing multiple patches/devices, so that there is more tolerance for the relative positioning of patch 122 or other external device and the lens 118. There could be an automated process that monitors signal strength and automatically adjusts which laser transceiver(s) in the patch(es) are used to communicate with the implant 110 via the lens 118 and fiber 116.

Figure 14:
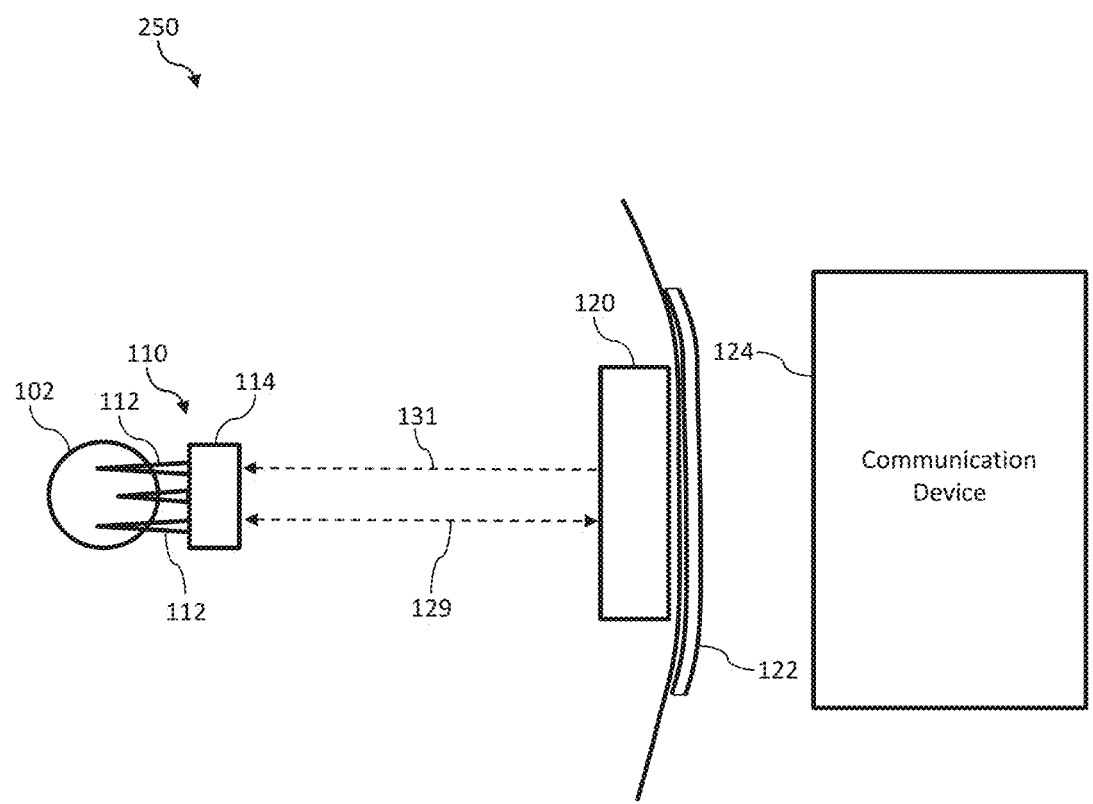
FIG. 14 is a diagram of an exemplary neuromodulation system according to embodiments of the present disclosure.

Referring now to FIG. 14, shown therein is a diagram of an exemplary neuromodulation system 250 according to embodiments of the present disclosure. In that regard, the neuromodulation system 230 is similar in many respects to the neuromodulation systems 100, 160, 164, and 230 of FIGS. 1, 2, 7, 8, and 13. However, in the neuromodulation system 250 of FIG. 14, the internal relay 120 may transmit power and/or data to the implantable neuromodulation module 110 using IR communications without the use of an optical fiber. For example, FIG. 14 shows power being transmitted to the implantable neuromodulation module 110, as indicated by arrow 131, and two-way communication of data between the internal relay 120 and the neuromodulation module 110, as indicated by arrow 129. In this manner, both data 129 and power 131 can be transmitted to the implantable neuromodulation module 110 without the need to also implant an optical fiber. However, in some implementations the neuromodulation system 250 is configured to only provide stimulation and not monitoring, thereby eliminating the need for two-way communication between the implantable neuromodulation module 110 and the internal relay 120.

The data and power may be transmitted from the internal relay 120 to the implantable neuromodulation module 110 sequentially and/or simultaneously. For example, power may be transmitted and then data may be transmitted. As another example, power may be transmitted at one wavelength (or range of wavelengths), while data is transmitted at another wavelength (or range of wavelengths). The implantable neuromodulation module 110 may include one or more optical filters to filter the power and/or data such that the appropriate wavelength(s) is received at the corresponding receiver(s) of the implantable neuromodulation module 110. In some instances, the implantable neuromodulation module 110 can include a lens, such as lens 118, to facilitate receiving IR signals (power and/or data) from the internal relay 120 and/or transmitting IR signals to the internal relay 120.

The internal relay 120 (or the communication device 124 and/or patch 122 in communication with the internal relay 120) can adjust the strength of the power and/or data signals 129, 131 transmitted to the neuromodulation module 110 to account for the location of the implantable neuromodulation module 110 within the patient. For example, the strength of the power and/or data signals 129, 131 can be adjusted by varying the power, wavelength, pulse profile (e.g., pulsed or continuous wave), etc. to account for the location of the implantable neuromodulation module 110 relative to the internal relay, including the distance between the components and/or the type(s) of medium (bone, tissue, nerve, bodily fluids, etc.) between the components. In this regard, the internal relay 120 (or the communication device 124 and/or patch 122 in communication with the internal relay 120) can ensure that the power signal received by the implantable neuromodulation module 110 is sufficient to drive the stimulation pulses of the electrodes 112 in accordance with a desired stimulation profile. In that regard, the stimulation profile may be predefined for the implantable neuromodulation module 110 such that the implantable neuromodulation module 110 executes the same stimulation profile over time. In other instances, the stimulation profile can be updated from time to time. For example, in some instances the implantable neuromodulation module 110 includes rewriteable memory that stores the stimulation profile such that the memory can be updated wirelessly, as needed, to update the stimulation profile. For example, in some instances the data transmitted from the internal relay 120 to the implantable neuromodulation module 110 includes the stimulation profile that is to be executed by the implantable neuromodulation module 110.

Information and signals may be represented using any of a variety of different technologies and techniques in accordance with the present disclosure. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). The implant could contain a programmable device (CPU with nonvolatile memory, FPGA, etc.) where the communication could program a particular stimulation therapy that does not require communication from outside of the body, but could be updated periodically (with communication from outside the body) to improve the therapy.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of [at least one of A, B, or C] means A or B or C or AB or AC or BC or ABC (i.e., A and B and C).

As those of some skill in this art will by now appreciate and depending on the particular application at hand, many modifications, substitutions and variations can be made in and to the materials, apparatus, configurations and methods of use of the devices of the present disclosure without departing from the spirit and scope thereof. In light of this, the scope of the present disclosure should not be limited to that of the particular embodiments illustrated and described herein, as they are merely by way of some examples thereof, but rather, should be fully commensurate with that of the claims appended hereafter and their functional equivalents.

What is claimed is:

1. A neuromodulation system, comprising:
   an implantable module in communication with an optical fiber, the implantable module including:
      a photodiode in optical communication with the optical fiber, the photodiode configured to receive light from the optical fiber and generate electrical current in response to receiving the light from the optical fiber;
      a first optical transceiver in optical communication with the optical fiber, the first optical transceiver configured to receive data from the optical fiber and transmit data to the optical fiber; and
      at least one electrode configured to provide electrical stimulation to a nerve utilizing the electrical current generated by the photodiode; and
   an implantable relay module including:
      a radio frequency transceiver configured to communicate with a communications device outside of a patient body; and
      a second optical transceiver in optical communication with the implantable module via the optical fiber.

2. The neuromodulation system of claim 1, further comprising the optical fiber.

3. The neuromodulation system of claim 2, wherein the optical fiber is mechanically coupled to the implantable module.

4. The neuromodulation system of claim 2, wherein the optical fiber is spaced from and independently positionable relative to the implantable module.

5. The neuromodulation system of claim 2, wherein:
   the light received by the photodiode from the optical fiber to generate the electrical current is at a first wavelength;
   the data received by the first optical transceiver from the optical fiber is at a second wavelength, the second wavelength being different than the first wavelength; and
   the photodiode is transparent to light of the second wavelength.

6. The neuromodulation system of claim 5, further comprising an optical filter positioned between the photodiode and the first optical transceiver.

7. The neuromodulation system of claim 1, wherein the implantable relay module further includes an infrared light source.

8. The neuromodulation system of claim 7, wherein the second optical transceiver of the implantable relay module includes the infrared light source.

9. The neuromodulation system of claim 7, wherein the second optical transceiver of the implantable relay module includes a light source separate from the infrared light source.

10. The neuromodulation system of claim 1, wherein the implantable module further includes a temporary power storage unit for storing the electrical current generated by the photodiode.

11. The neuromodulation system of claim 10, wherein the temporary power storage unit includes a capacitor.

12. The neuromodulation system of claim 1, wherein the implantable module further includes a processing unit, the processing unit configured to process the data received by the first optical transceiver, wherein the data received by the processing unit includes a stimulation profile and wherein the processing unit is further configured to selectively activate the at least one electrode based on the stimulation profile.

13. The neuromodulation system of claim 12, wherein the stimulation profile includes at least one of a spatial stimulation pattern or a temporal stimulation pattern.

14. The neuromodulation system of claim 1, further comprising an infrared (IR) light source.

15. The neuromodulation system of claim 14, wherein the IR light source is part of an external laser source.

16. The neuromodulation system of claim 14, wherein the IR light source is part of an internal relay.

17. The neuromodulation system of claim 2, wherein the optical fiber includes a lens configured to optically couple the optical fiber to the second optical transceiver while being spaced from and independently positionable relative to the implantable relay module.

18. A system comprising:
an implantable module that includes:
a photodiode to receive light and to generate electrical power in response to the light;
a power storage unit coupled to the photodiode to store the electrical power generated by the photodiode; and
an electrode to provide electrical stimulation to a nerve using the electrical power generated by the photodiode; and
an implantable relay module for optical communication with the implantable module and including:
a radio frequency transceiver configured to communicate with a communications device outside of a patient body.

19. The system of claim 18, wherein the implantable module further includes an optical fiber optically coupled to the photodiode to conduct the light to the photodiode.

20. The system of claim 18, wherein the implantable module further includes:
an optical transceiver to provide data; and
a processing unit coupled to the optical transceiver to receive the data, wherein the electrode is to provide the electrical stimulation to the nerve in response to the received data.

21. The system of claim 20, wherein the light received by the photodiode has a first wavelength and light used by the optical transceiver to provide the data has a second wavelength that is different from the first wavelength.

* * * * *